United States Patent
Brady

(10) Patent No.: US 9,636,213 B2
(45) Date of Patent: May 2, 2017

(54) DEFORMABLE INTRAOCULAR LENSES AND LENS SYSTEMS

(75) Inventor: Daniel G. Brady, San Juan Capistrano, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 1677 days.

(21) Appl. No.: 11/241,586

(22) Filed: Sep. 30, 2005

(65) Prior Publication Data

US 2007/0078515 A1   Apr. 5, 2007

(51) Int. Cl.
*A61F 2/16* (2006.01)

(52) U.S. Cl.
CPC .......... *A61F 2/1613* (2013.01); *A61F 2/1635* (2013.01); *A61F 2/1648* (2013.01); *A61F 2250/0018* (2013.01)

(58) Field of Classification Search
CPC ..... A61F 2/1613; A61F 2/1635; A61F 2/1648
USPC ............ 623/4.1, 6.11, 6.13, 6.14, 6.23, 6.24, 623/6.27, 6.3–6.32, 6.34, 6.37–6.4, 6.43, 623/6.56, 6.22, 6.39
See application file for complete search history.

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |

(Continued)

FOREIGN PATENT DOCUMENTS

| | | |
|---|---|---|
| AU | 3225789 | 10/1989 |
| CH | 681 687 A5 | 5/1993 |

(Continued)

OTHER PUBLICATIONS

U.S. Appl. No. 10/280,918, filed Aug. 5, 2003.

(Continued)

*Primary Examiner* — Corrine McDermott
*Assistant Examiner* — Joshua Levine
(74) *Attorney, Agent, or Firm* — Abbott Medical Optics Inc.

(57) ABSTRACT

An intraocular lens includes a deformable optic, a rigid optic, and a support structure. The deformable optic is disposed about an optical axis and comprises a solid material and a deformable surface. The rigid optic is disposed about the optical axis and comprises a solid material and a rigid surface. The support structure is operably coupled to at least one of the optics for pressing the deformable surface and the rigid surface together in response to or in the absences of an ocular force, whereby at least a portion of the deformable surface changes shape such that the optical power of the at least a portion of the deformable surface and/or the intraocular lens changes by at least 2 Diopter.

20 Claims, 6 Drawing Sheets

(56) References Cited

U.S. PATENT DOCUMENTS

| | | |
|---|---|---|
| 3,431,327 A | 3/1969 | Tsuetaki |
| 3,482,906 A | 12/1969 | Volk |
| 3,542,461 A | 11/1970 | Girard et al. |
| 3,673,616 A | 7/1972 | Federov et al. |
| 3,693,301 A | 9/1972 | Lemaltre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzacco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsnetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | DeCarle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A * | 1/1990 | Turley ........................ 623/6.13 |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Milge et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |

(56) References Cited

U.S. PATENT DOCUMENTS

| | | |
|---|---|---|
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Meneles et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |

(56) References Cited

U.S. PATENT DOCUMENTS

| | | |
|---|---|---|
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skottun et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 * | 5/2003 | Green ........................ 623/6.34 |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 * | 7/2003 | Weinschenk et al. ....... 623/6.34 |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,685,315 B1 | 2/2004 | De |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,942,695 B1 | 9/2005 | Chapoy et al. |
| 7,018,409 B2 | 3/2006 | Glick et al. |
| 7,025,783 B2 | 4/2006 | Brady et al. |
| 7,097,660 B2 | 8/2006 | Portney |
| 7,125,422 B2 | 10/2006 | Woods |
| 7,150,759 B2 | 12/2006 | Paul et al. |
| 7,179,292 B2 | 2/2007 | Worst et al. |
| 7,220,279 B2 | 5/2007 | Nun |
| 7,223,288 B2 | 5/2007 | Zhang et al. |
| 7,503,938 B2 | 3/2009 | Phillips |
| 7,815,678 B2 | 10/2010 | Ben Nun |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0103536 A1 | 8/2002 | Landreville et al. |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0151973 A1 * | 10/2002 | Arita et al. ................... 623/6.22 |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 * | 6/2003 | Glazier ........................ 623/6.13 |
| 2003/0109925 A1 * | 6/2003 | Ghazizadeh et al. ........ 623/6.34 |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0149480 A1 * | 8/2003 | Shadduck ..................... 623/6.41 |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Mebner et al. |
| 2004/0230299 A1 | 11/2004 | Simpson et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 * | 1/2005 | Shadduck ..................... 623/6.35 |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0125056 A1 | 6/2005 | Deacon et al. |

(56) References Cited

U.S. PATENT DOCUMENTS

| | | |
|---|---|---|
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0288785 A1 | 12/2005 | Portney et al. |
| 2006/0064162 A1 | 3/2006 | Klima |
| 2006/0111776 A1 | 5/2006 | Glick et al. |
| 2006/0116765 A1 | 6/2006 | Blake et al. |
| 2006/0238702 A1 | 10/2006 | Glick et al. |
| 2007/0078515 A1 | 4/2007 | Brady |
| 2007/0100444 A1 | 5/2007 | Brady et al. |
| 2007/0106381 A1 | 5/2007 | Blake |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2007/0299487 A1 | 12/2007 | Shadduck |
| 2008/0161913 A1 | 7/2008 | Brady |
| 2008/0161914 A1 | 7/2008 | Brady |
| 2009/0012609 A1 | 1/2009 | Geraghty |

FOREIGN PATENT DOCUMENTS

| | | |
|---|---|---|
| CH | 681687 A5 | 5/1993 |
| DE | 2702117 | 7/1978 |
| DE | 2702117 A1 | 7/1978 |
| DE | 3246306 | 6/1984 |
| DE | 3246306 A1 | 6/1984 |
| DE | 4038088 | 6/1992 |
| DE | 4038088 A1 | 6/1992 |
| DE | 19501444 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 0064812 | 11/1982 |
| EP | 0246216 | 11/1987 |
| EP | 0328117 | 8/1989 |
| EP | 0329981 | 8/1989 |
| EP | 0337390 | 10/1989 |
| EP | 0342895 | 11/1989 |
| EP | 0351471 | 1/1990 |
| EP | 0 356 050 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 0488835 | 6/1992 |
| EP | 492126 A2 | 7/1992 |
| EP | 0507292 | 10/1992 |
| EP | 0 766 540 B1 | 4/1993 |
| EP | 0566170 | 10/1993 |
| EP | 0601845 | 6/1994 |
| EP | 605841 A1 | 7/1994 |
| EP | 0691109 | 1/1996 |
| EP | 766540 A1 | 4/1997 |
| EP | 779063 A1 | 6/1997 |
| EP | 780718 A1 | 6/1997 |
| EP | 0897702 | 2/1999 |
| EP | 0766540 B1 | 4/1999 |
| EP | 1108402 A2 | 6/2001 |
| EP | 1321112 A1 | 6/2003 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 0211134 | 1/1990 |
| JP | 2126847 | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 9109336 A1 | 6/1991 |
| WO | WO 93/05733 | 1/1993 |
| WO | 9302639 A1 | 2/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 9635398 A1 | 11/1996 |
| WO | 97/12272 | 4/1997 |
| WO | 97/27825 | 8/1997 |
| WO | 97/43984 | 11/1997 |
| WO | 9805273 A1 | 2/1998 |
| WO | 9821621 A1 | 5/1998 |
| WO | 9849594 A1 | 11/1998 |
| WO | 98/56315 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 00/61036 | 4/2000 |
| WO | 0021467 A1 | 4/2000 |
| WO | 00/27315 | 5/2000 |
| WO | 0035379 A1 | 6/2000 |
| WO | 0046629 A1 | 8/2000 |
| WO | 0059407 A1 | 10/2000 |
| WO | 00/66039 | 11/2000 |
| WO | 0066037 A1 | 11/2000 |
| WO | 0066040 A1 | 11/2000 |
| WO | 0066041 A1 | 11/2000 |
| WO | 0108605 A1 | 2/2001 |
| WO | 01/19288 | 3/2001 |
| WO | 0119289 A1 | 3/2001 |
| WO | 0128144 A1 | 4/2001 |
| WO | 01/34066 | 5/2001 |
| WO | 01/34067 | 5/2001 |
| WO | 0134061 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | WO 02/19949 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03015657 A2 | 2/2003 |
| WO | WO 03/015669 | 2/2003 |

(56) References Cited

FOREIGN PATENT DOCUMENTS

| | | |
|---|---|---|
| WO | 03/034949 | 5/2003 |
| WO | 03049646 A2 | 6/2003 |
| WO | 03/059208 | 7/2003 |
| WO | 03057081 A2 | 7/2003 |
| WO | 03059196 A2 | 7/2003 |
| WO | 03/075810 | 9/2003 |
| WO | 03084441 A1 | 10/2003 |
| WO | 03092552 A1 | 11/2003 |
| WO | 04000171 A1 | 12/2003 |
| WO | 2004020549 A1 | 3/2004 |
| WO | 2004037127 A2 | 5/2004 |
| WO | 2004073559 A1 | 9/2004 |
| WO | 2005011531 A2 | 2/2005 |
| WO | 2005019871 A2 | 3/2005 |
| WO | WO 2005/018504 A1 | 3/2005 |
| WO | 03082147 A3 | 8/2005 |
| WO | 2005084587 A2 | 9/2005 |
| WO | WO2005115278 A1 | 12/2005 |
| WO | 2007/040964 | 4/2007 |
| WO | 2007/067872 | 6/2007 |
| WO | 2007-067872 | 6/2007 |
| ZA | 888414 | 10/1988 |

OTHER PUBLICATIONS

U.S. Appl. No. 10/280,937, filed Oct. 25, 2005.
Fechner et al. Iris-claw lens in phakic eyes to correct hyperopia: preliminary study. *J. Cataract Refract. Surg.*, 24, Jan. 1998.
Mandell, *Contact Lens Practice*, 4$^{th}$ Ed.
Menezo et al. Endothelial study of iris-claw phakic lens: four year follow-up. *J. Cataract Refract. Surg.*, 24, Aug. 1998.
Thornton, *Accommodation in Pseudophakia*, 25, p. 159.
AMO Specs, Model AC-21B, 1992.
Study Design of Nuvita, Mar. 20, 1997.
Program from ASCRS Symposium showing video tape between Apr. 10-14, 1999.
DVD titled "New elliptical accommodative IOL for cataract surgery" shown at ASCRS Symposium on Apr. 10, 1999.
Hecht et al., "Optics", 4$^{th}$ ed., pp. 188-190, 1979.
Taylor, "The International System of Units (SI)," NIST Special Publication 330, p. 15, Aug. 1991.
English translation of WO 93/05733 A1.
U.S. Appl. No. 09/656,661, filed Sep. 7, 2000.
U.S. Appl. No. 09/721,072, filed Nov. 22, 2000.
Altan-Yaycioglu R., et al., "Pseudo-accommodation with Intraocular Lenses Implanted in the Bag," Journal of Refractive Surgery, 2002, vol. 18 (3), pp. 271-275.
Chauvin-Opsia, Azurite ACL (0459).
Chiron, Clemente Optfit Model SP525, Brochure Translation, Jul. 12, 1998.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, Jul. 1, 1992, vol. 31(19), pp. 3750-3754.
Foldable Intraocular Lens Implants and Small Incision Cataract Surgery, Ohio Valley Eye Physicians, 2004.
Hanita Lenses, Source Ocular Surgery News International, 1 page.
Hara T., et al., "Accommodative Intraocular Lens with Spring Action Part 1 Design and Placement in an Excised Animal Eye," Ophthalmic Surgery, 1990, vol. 21(2), pp. 128-133.
Holladay J.T., et al., "Analysis of Edge Glare Phenomena in Intraocular Lens Edge Designs," Journal of Cataract and Refractive Surgery, 1999, vol. 25 (6), pp. 748-752.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70(6), pp. 439-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracorneal Lenses," International Ophthalmology Clinics, 1991, vol. 31(1), pp. 37-46.
Marron J.C., et al., "Higher-order Kinoforms," Computer and Optically Formed Holographic Optics, 1990, vol. 1211, pp. 62-66.
McCarey B.E., et al., "Modeling Glucose Distribution in the Cornea," Current Eye Research, 1990, vol. 9 (11), pp. 1025-1039.
Mediphacos Ltda, Ocular Surgery News International.
Opthalmed Inc., OMAC-260.
Prosecution History for U.S. Appl. No. 10/958,871 (US20050234547) filed on Oct. 5, 2004.
Prosecution History for U.S. Appl. No. 11/057,705 (US20060184244) filed on Feb. 14, 2005.
Prosecution History for U.S. Appl. No. 11/195,422 (US20050267575) filed on Aug. 1, 2005.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Storz Opthalmics Inc., Model L122UV ACL.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31(11), pp. 2172-2179.
Universe IOL Center, Ocular Surgery News International.
Video presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
World Optics Inc., Ophthalmology Times, Mar. 15, 1995.

\* cited by examiner

DEFORMABLE INTRAOCULAR LENSES AND LENS SYSTEMS

BACKGROUND OF THE INVENTION

Field of the Invention

This invention relates generally to intraocular lenses and intraocular lens systems, and more specifically to deformable intraocular lenses and lens systems for providing accommodation.

Description of the Related Art

Monofocal intraocular lenses are now commonly used to restore vision lost, for example, due to the formation of cataracts. More recent efforts in the field have concentrated on restoring or simulating accommodation, the ability of the eye to provide both near vision and distant vision. One approach to providing accommodation for an eye in which the natural lens has been removed is to use a bifocal or multifocal lens that simultaneously produces two or more foci. For example, a refractive lens surface may be produced in which different portions of the surface have different focal lengths, for example, as taught by Portney in U.S. Pat. No. 5,225,858. Alternatively, Cohen teaches in U.S. Pat. No. 5,121,979, the use of a bifocal lens comprising a diffractive phase plate in which the entire lens produces two different foci corresponding to two different diffractive orders. Bifocal lenses utilize the ability of a subject's brain to give preference to the focus corresponding to a selected image.

Another approach is to provide an intraocular lens that is directly responsive to the ciliary muscle of the eye. For example, in U.S. Pat. No. 6,551,354, an intraocular lens is used to produce accommodation by providing an optic that moves in the anterior direction when the ciliary muscle contracts. In U.S. Pat. No. 6,616,692, herein incorporated by reference, a first optic having a negative optical power is combined with a second optic having a higher optical power than the first optic. The combination of the first and second optic advantageously reduces the amount of axial movement in the eye needed to provide accommodation for intermediate and near vision.

In another approach, accommodation is provided by using ciliary muscle contraction to deform at least a portion of the intraocular lens optic. One potential problem with this approach is that the shape of the optic surface produced during accommodation may result in undesirable amounts of optical aberrations, for example, spherical aberrations.

Accommodating intraocular lenses are needed that easily and effectively deform and change shape to provide both distant vision and near vision in a way that provides design flexibility and/or reduces optical aberrations.

SUMMARY OF THE INVENTION

Embodiments of the invention are generally directed to devices and methods for providing ocular accommodation and more specifically to ophthalmic devices such as intraocular lenses for changing the shape of or deforming at least a portion of a deformable optic surface when pressed together with and/or separated from the surface of another optic or a surface of the capsular bag. Such ophthalmic devices may be configured to easily and effectively deform and change shape to provide both distant vision and near vision in a way that provides design flexibility and/or reduces optical aberrations. Embodiments of the invention also include devices and methods for providing more than one focus, reducing at least one optical aberration, and/or producing other desired optical effects when the deformable optic surface is either pressed together or separated from another optic or a surface of the capsular bag.

In one aspect of the invention, an intraocular lens comprises a deformable optic, a rigid optic and a support structure. The deformable optic is disposed about an optical axis and comprises a solid material and a deformable surface. The rigid optic is disposed about the optical axis and comprises a solid material and a rigid surface. The support structure is operably coupled to at least one of the optics and is configured for pressing the deformable surface and the rigid surface together in response to an ocular force, whereby at least a portion of the deformable surface changes shape such that optical power of at least a portion of the deformable surface and/or intraocular lens changes, typically by at least 1 Diopter, preferably between about 2 to about 5 Diopters. Alternatively, the support structure may be operably coupled to at least one of the optics for pressing the deformable surface and the rigid surface together in the absence of ocular forces. In certain embodiments, at least a portion of the deformable surface is the entire surface or substantially the entire surface forming a clear aperture of the deformable surface. The intraocular lens is preferably configured to have an accommodative bias or a disaccommodative bias; however, may alternatively be configured to have neither an accommodative bias nor a disaccommodative bias.

At least one of the optics may be configured to have substantially no optical power, to have a single optical power, or to provide two or more optical powers or focal points. At least one of the optics may have an aspheric surface and/or have a multifocal and/or diffractive surface. The rigid optic may be used to either increase or decrease radius of curvature of the deformable surface when the surfaces are pressed together. The rigid optic may be configured for placement against the posterior capsule of an eye and to maintain a substantially fixed shape. The rigid surface may be configured to reduce an optical aberration of at least one of the deformable optic, the intraocular lens, and the eye when the surfaces are pressed together.

The deformable optic may be configured to have either an accommodative bias or a disaccommodative bias. The deformable optic has a center thickness along the optical axis when the in a substantially unstressed state that may change as the rigid and deformable optics are pressed together. For example the deformable optic may be adapted to change the center thickness by a factor of at least 1.1 when the ocular force is in the range of about 1 to 9 grams. In another example, the deformable optic adapted to change the center thickness by at least 100 micrometers when the ocular force is in the range of about 1 to 9 grams. The deformable optic may be made of a first material and the rigid optic is made of a second material, wherein at least one of the refractive index and the Abbe number of the first material is different from that of the second material. As used herein, the term "accommodative bias" refers to an intraocular lens that is configured to provide near to intermediate vision when in a natural or unstressed state (e.g., with no ocular force or other external forces on a support structure of the intraocular lens). By contrast, the term "disaccommodative bias" refers to the state of an intraocular lens that is configured to provide distant vision when in a natural or unstressed state. As used herein, the terms "Abbe Number" means an optical dispersion property of a material defined as $$V = \frac{n_D - 1}{n_F - n_C},$$

where $n_D$, $n_F$, $n_C$ are the refractive indices of the material at the wavelengths of the 589.2 nanometers, 486.1 nanometers, and 656.3 nanometers, respectively. As used herein a force or ocular force in number of "grams" means a force having a value in that number of kilograms-force divided by 1000, which in units of Newtons is equal to the number of grams of force times $9.80665 \times 10^{-3}$.

The intraocular lens may further comprise a stiffening layer that is stiffer than the deformable optic, where the deformable optic is typically disposed between the stiffening layer and the rigid optic. In such embodiment, the deformable optic may be made of a first material and the stiffening layer is made of a second material, wherein at least one of the refractive index and the Abbe number of the first material is different than that of the second material. Additionally or alternatively, the deformable optic may further comprise a relief portion for providing a volume into which material from the deformable optic may expand or enlarge when the deformable surface is deformed. The relief portion may comprise at least a portion of a periphery about the deformable optic and/or one or more voids within the deformable optic.

The support structure may be configured for placement in at least one of the sulcus and the capsular bag. The support structure may comprise one or more haptics. Alternatively or additionally, the support structure may comprise an optic positioning element having an anterior segment configured for yieldable engagement with an anterior capsule of an eye, a posterior segment for yieldable engagement with a posterior capsule of the eye, and an equatorial segment disposed between the anterior segment and the posterior segment. In such embodiments, the support structure may be constructed to substantially maintain the equatorial segment in contact with an equatorial portion of the capsule in response to the ocular force. The rigid optic in such embodiments is typically operably coupled at an opening in the anterior segment substantially centered about the optical axis. The rigid optic and the deformable optic may be configured to have one or more overlapping openings that allow fluid to flow into and out of the interior of the optic positioning element.

In another aspect of the invention, an intraocular lens comprises a deformable optic, a rigid optic and a support structure, wherein the support structure is operably coupled to at least one of the optics for producing a force that presses the deformable surface and the rigid surface together in the response to an ocular force such that at least a portion of the deformable surface is deformed and substantially conforms to the shape of the rigid surface.

In yet another aspect of the invention only a portion of the deformable surface changes shape. In such embodiments, the portion of the deformable optic may be a central portion of the deformable optic with a diameter that is typically greater than about 2 mm. Alternatively, the deformable optic is a peripheral portion of the deformable optic that typically is concave and typically has an inner diameter that is less than about 4 mm. In still another aspect of the invention, the intraocular lens does not comprise a rigid optic and the support structure is operably coupled to the deformable optic for pressing the deformable surface and at least one surface of the capsular bag of an eye together in response to an ocular force, whereby at least a portion of the deformable surface changes shape.

In one aspect of the invention, a method of providing accommodation comprises providing an intraocular lens according to an embodiment of the present invention and implanting the intraocular lens into the eye of a subject. The method further comprises configuring the support structure of the intraocular lens for pressing the deformable surface and the rigid surface together in response to or in the absence of an ocular force, whereby at least a portion of the deformable surface changes shape such that optical power of the at least a portion of the deformable surface and/or the intraocular lens changes. The method may additionally comprise configuring the intraocular lens such that the radius of curvature of the deformable surface increases or decreases in response to the ocular force while the radius of curvature of the rigid surface remains substantially fixed. The method may also comprise configuring the intraocular lens so that an optical aberration of at least one of the deformable optic, the intraocular lens, and the eye is reduced in the response to the ocular force. The method may further comprise configuring the intraocular lens so that the deformable surface changes from a substantially spherical surface to an aspheric surface as the surfaces are pressed together or when the surfaces or separated. The method may also comprise configuring the intraocular lens so that the deformable surface changes from a first radius of curvature to a second radius of curvature different from the first radius of curvature when the surfaces are pressed together.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 15 figures, with like numerals indicating like parts.

DETAILED DESCRIPTION OF THE DRAWINGS

Figure 1:
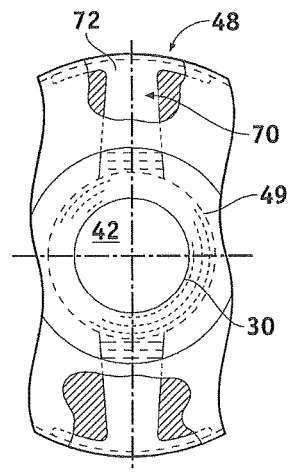
FIG. 1 is a front view of accommodative intraocular lens (IOL) according to a first embodiment of the invention.
Figure 2:
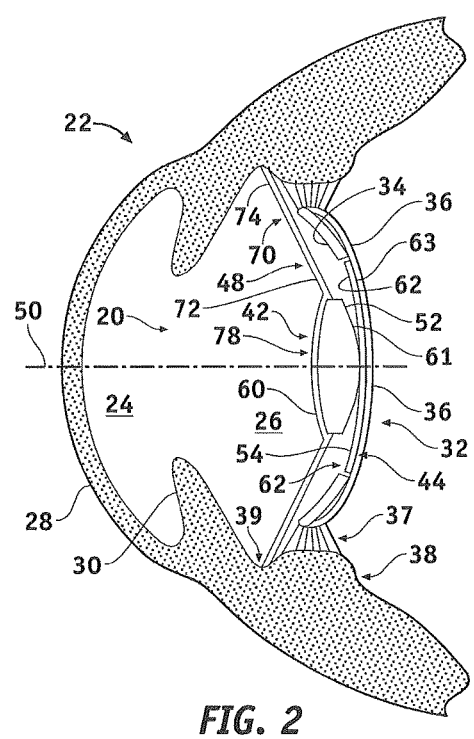
FIG. 2 is a side view of the accommodative IOL illustrated in FIG. 1 shown within an eye in an accommodative state.

Referring to FIGS. 1 and 2, in certain embodiments, an intraocular lens (IOL) 20 is configured for placement within a mammalian eye 22, preferably that of a human subject. Before providing a more detailed description of the structure and function of the IOL 20, a brief overview of the eye 22 will be given. The eye 22 may be divided into an anterior chamber 24 and a posterior chamber 26. The anterior chamber 24 includes a volume within the eye 22 that is substantially defined by a cornea 28 and an iris 30. The posterior chamber 26 contains a capsular bag 32 comprising an anterior capsule 34 and a posterior capsule 36. Prior to implantation of the IOL 20 into the eye 22, the capsular bag 32 has a substantially discoid shape that is defined by a natural lens (not shown). During surgery, an opening is formed in the anterior capsule 34 through which the natural lens is removed.

The posterior chamber 26 may be defined as the volume within the eye 22 that is disposed between the iris 30 and the posterior surface 36 of the capsular bag 32. The capsular bag 32 is surrounded by a series of zonular fibers (called zonules) 37 that are disposed between and connect the capsular bag 32 and a ciliary muscle 38. The posterior chamber 26 also contains a sulcus 39, a region around a perimeter of the posterior chamber 26 that is disposed between the iris 30 and the ciliary muscle 38.

The cornea 28 may be used in combination with either the natural lens (prior to surgery) or the IOL 20 (after surgery) to form images on the retina (not shown) of the eye 22. When the natural lens is present, the shape and position of the capsular bag 32 is used to adjust the amount of optical power produced by the eye 22, thus allowing the subject to focus on both relatively near and relatively distant objects. In order to accommodate or focus on relatively near objects, ocular forces are produced by contraction of the ciliary muscle 38 that release the tension on zonules 37 and allow the capsular bag 32 and the natural lens to obtain a more oval shape.

As used herein, the term "ocular force" means any force produced by the eye of a subject that stresses, moves, or changes the shape of the natural lens of the eye or of at least a portion of an intraocular lens that is placed into the eye of a subject. The ocular force acting on the lens (either a natural lens or an IOL) may be produced, for example, by the state or configuration of the ciliary body. (e.g., contracted or retracted), changes in the shape of the capsular bag, stretching or contraction of one or more zonules, vitreous pressure, and/or movement of some part of the eye such as the ciliary body, zonules, or capsular bag, either alone or in combination.

The ocular force acting on the IOL 20 may be produced when the ciliary muscle 38 is either contracted or retracted, depending upon the design of the IOL 20 and/or the state of the eye 22 when the IOL 20 is implanted into and secured within the eye 22 (e.g., an accommodative state or a disaccommodative state). For example, the IOL 20 may be configured to provide near vision to a subject when the IOL 20 is in a natural or unstressed state and an ocular force is produced on the IOL 20 when the ciliary muscle 38 is retracted. In such embodiments, an ocular force may be used to stress the IOL 20 in order to produce a disaccommodative state in which the eye 22 is able to focus on distant or intermediate objects. In another example, the IOL 20 may be configured to provide distant vision when in a natural state and an ocular force is produced when the ciliary muscle 38 is contracted. In such embodiments, an ocular force may be used to stress the IOL 20 in order to produce an accommodative state in which the eye 22 is able to focus on relatively near objects. As used herein, the terms "natural state" or "unstressed state" of an IOL are used interchangeably and mean a condition of an IOL in which there are no or substantially no ocular force or other external forces on the IOL 20, with the exception of residual forces such as gravitational forces.

For the human eye, the ocular force is preferably in the range of about 0.1 to 100 grams, more preferably in the range of about 1 to 9 grams, and even more preferably in the range of about 6 to 9 grams. In certain embodiments, the ocular force produced by the eye is in the range of about 1 to 3 grams. These preferred ranges are based on current physiology understanding of the human eye and are not meant to limit the scope of embodiments of the present invention. The magnitude an ocular force available for stressing the natural lens and/or the IOL 20 will, of course, vary between individual subjects based, for instance, on such factors as age of the subject, disease conditions, and the physiologic construction of the eye. It is anticipated that as the understanding of the physiology of the human and mammalian eye within the field increases, the preferred range or ranges of operation for embodiments of the present invention will be more precisely defined.

Figure 3:
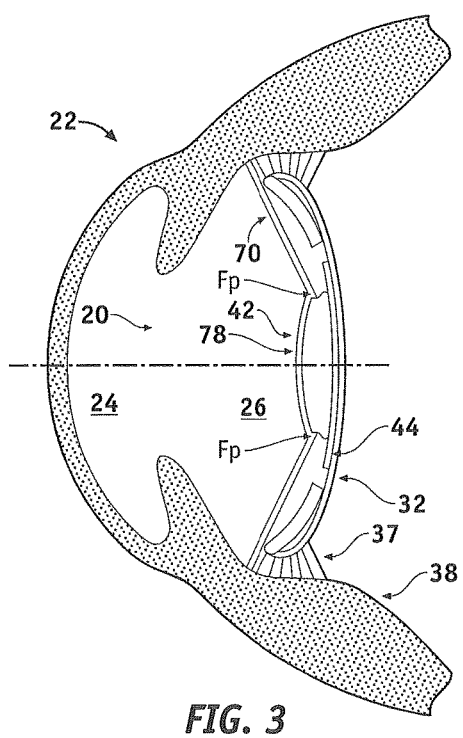
FIG. 3 is a side view of the accommodative IOL illustrated in FIG. 1 shown within an eye in a disaccommodative state.

Referring to FIGS. 1-3, in one useful embodiment of the present invention, the IOL 20 may be used to provide accommodative and disaccommodative vision to a subject. The IOL 20, comprises a deformable optic 42, a rigid optic 44, and a support structure 48. The deformable optic 42 is disposed about an optical axis 50 and comprises a deformable surface 52 and a periphery 49. The rigid optic 44 is disposed about the optical axis 50 and further comprises a rigid surface 54. The deformable optic 42 also comprises an anterior surface 60 and posterior surface 61, while the rigid optic 44 additionally comprises an anterior surface 62 and posterior surface 63. In the illustrated embodiment, the posterior surface 61 of the deformable optic 42 is the deformable surface 52 and the anterior surface 62 of the rigid optic 44 is the rigid surface 54.

The IOL 40 and the deformable optic 42 may be configured to have a disaccommodative bias, as illustrated in FIG. 2. Alternatively, the IOL 40 may have an accommodative bias, depending upon various factors such as the particular physiology of eye 22 and the particular operational outcome desired by the practitioner and/or designer. As used herein, the term "accommodative bias" refers to an intraocular lens that is configured to provide near to intermediate vision when in a natural or unstressed state (e.g., with no ocular force or other external forces on the support structure 148). By contrast, the term "disaccommodative bias" refers to the state of an intraocular lens wherein an optic and/or IOL are configured to provide distant vision when in a natural or unstressed state.

The support structure 48 is operably coupled to the deformable optic 42, but in other embodiments may be operably coupled to the rigid optic 44 or to both the deformable optic 42 and the rigid optic 44. In certain embodiments, the support structure 48 is configured for pressing the deformable surface 52 of the deformable optic 42 and the rigid surface 54 of the rigid optic 44 together in response to or in the presence of an ocular force, wherein at least a portion of the deformable surface 52 changes shape such that the optical power of the at least a portion of the deformable surface 52 and/or the IOL 20 changes, typically by at least about 1 Diopter, preferably by at least 2 Diopters, more preferably by 3 Diopters, and even more preferably by at least 4 or 5 Diopters. In certain embodiments, the support structure 48 produces a force $F_p$ that presses the deformable surface 52 and the rigid surface 54 together in the response to an ocular force such that at least a portion of the deformable surface 52 is deformed and substantially conforms to the shape of the rigid surface 54.

In other embodiments, the support structure 48 is configured for pressing the deformable surface 52 and the rigid surface 54 together in the absence of an ocular force, wherein at least a portion of the deformable surface 52 changes shape, such that the optical power of the at least a portion of the deformable surface 52 and/or the IOL 20 changes, typically by at least 1 or 2 Diopters or more compared to the optical power of the IOL 20 when the deformable surface 52 is in an undeformed state. In such embodiments, the IOL 20 is configured to produce an internal force or forces that press the deformable surface 52 and the rigid surface 54 together when there are no external force, such as an ocular force, acting of the IOL 20. The IOL is further configured so that application of an external force, such as an ocular force, opposes the internal force or forces produced by the IOL 20 such that the surfaces 52, 54 are no longer pressed together or are only partially pressed together.

Figure 4:
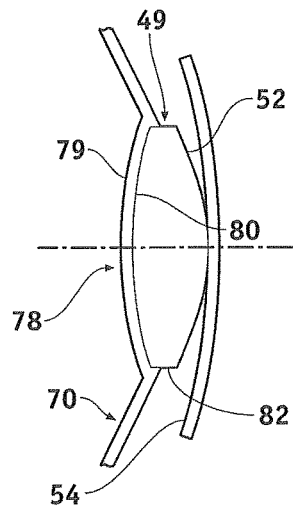
FIG. 4 is a magnified side view of the accommodative IOL illustrated in FIG. 2.
Figure 5:
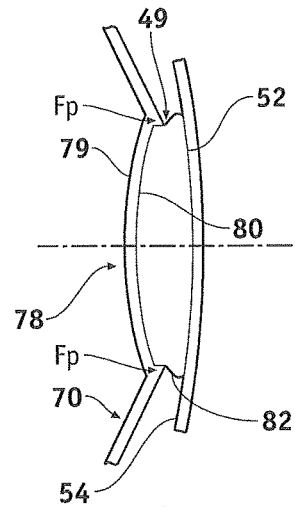
FIG. 5 is a magnified side view of the accommodative IOL illustrated in FIG. 3.

Referring to FIGS. 4 and 5, the deformable optic 42 may further comprise a relief portion 82 that is configured to provide a volume into which material from the deformable optic 42 may flow, enlarge or expand when the deformable surface 52 is deformed as it is pressed against the rigid surface 54. By providing a volume into which material may expand when the surfaces 52, 54 are pressed together, the relief portion 82 may be used to reduce the possibility that changes in the optical power produced by deformation of the deformable surface 52 are opposed or cancelled by a similar deformation in the opposite surface 60. The relief portion may comprise at least a portion of the periphery 49 about the deformable optic 42 that is not in contact with the support structure 48. For example, comparing FIGS. 4 and 5, the relief portion 82 is seen to comprise a portion of the periphery that is posterior to the haptic 70 and anterior to the rigid surface 54 of the rigid optic 44. The relief portion 82 is seen in FIG. 5 to bulge and fill with material from the deformable optic 42 when the deformable optic 42 is pressed against the rigid optic 44. In other embodiments, the relief portion 82 may comprise voids or opening within the body of the deformable optic 42 that also be used to allow fluid flow between the anterior and posterior portions of the anterior chamber 24 of the eye 22.

In certain embodiments, the deformable surface 52 is configured to be less stiff than the opposite surface 60 of the deformable optic 42. Similar to the relief portions 82, the greater stiffness of the opposite surface 60 be used to reduce the possibility that changes in the optical power produced by deformation of the deformable surface 52 are opposed or cancelled by a similar deformation in the opposite surface 60. The stiffness of the opposite surface 60 may be provided by operably coupling a stiffening coating or layer 78 to the deformable optic 42 that is made of a material that is harder or stiffer than the material from which other portions of the deformable optic 42 are made. Alternatively or additionally, the stiffening layer 78 may be integrally formed with the deformable optic 42 and/or the support structure 48 by hardening the opposite surface 60. The hardening may be accomplished, for example, by addition polymerization of the stiffening layer 78 over and above the amount of polymerization used in forming other portions of deformable optic 42. In the illustrated embodiment of FIGS. 1-5, the stiffening layer 78 is disposed in front of the anterior surface 60 of the deformable optic 42. More generally, the stiffening layer 78 is preferably disposed such that the deformable optic 42 is located between the stiffening layer 78 and the rigid optic 44.

In certain embodiments, the IOL 20 is configured for placement within the eye 22, for example within the sulcus 39, as illustrated in FIGS. 1-3. Alternatively, the IOL 20 may be configured for placement within another portion of the eye 22, for example within the capsular bag 32. The IOL 20 may be constructed of any of the commonly employed materials in the art, for example a silicone polymeric material, an acrylic polymeric material, a hydrogel forming polymeric material, such as polyhydroxyethylmethacrylate, polyphosphazenes, polyurethanes, and/or mixtures thereof. Combinations of the deformable optic 42, the rigid optic 44, and the support structure 48 may be the same material. Alternatively, each of these elements of the IOL 20 may be made of different materials. In certain embodiments, the entire IOL 20 is made of substantially the same material and is integrally formed to produce a compound structure for placement within the eye 22 as a single unit. Alternatively, one or more of the components of IOL 20 are made separately and assembled within the eye to form the IOL 20. Such a modular construction may advantageously allow the use of a smaller incision in the eye 22, thereby reducing healing time and general trauma to the eye 22.

In certain embodiments, the rigid optic 44 is disposed against or in contact with the posterior capsule 32, and the deformable optic 42 is disposed in front of or anterior to the rigid optic 44. In such embodiments, the deformable optic 42 is preferably configured to vault in a posterior direction (away from the cornea 28) so that it may be effectively pressed against the rigid optic 44 in response to or in the absence of an ocular force. The total optical power of the IOL 20 may be determined from the individual powers of the deformable optic 42 and the rigid optic 44 and may change depending on whether or not the deformable optic 42 and the rigid optic 44 are pressed together.

The optics 42, 44 may be constructed of any one or a combination of the commonly employed materials found in the art. For example, the rigid optic 44 may be of a relatively rigid material such as polymethylmethacrylate (PMMA), while the deformable optic 42 is made of one of the more resiliently deformable material found in the art, such as a silicone polymeric, an acrylic polymeric, a hydrogel-forting polymeric, or mixtures thereof. The material or materials used to form the optics 42, 44 are preferably optically clear optics that exhibit biocompatibility in the environment of the eye. The selection of suitable lens materials is well known to those of skill in the art. See, for example, David J. Apple, et al., Intraocular Lenses. Evolution, Design, Complications, and Pathology, (1989) William & Wilkins, herein incorporated by reference.

In certain embodiments, the deformable optic 42 and/or the rigid optic 44 are made of a solid material. As used herein, the term "solid" means a material that does not primarily comprise a gas or a liquid and/or that is a homogeneous material with the ability to maintain a substantially fixed surface, form, or shape in the presence of small external forces placed on an object made of such a material. The term "solid" includes gel materials such as hydrogel materials, hydrophilic material, and hydrophobic materials that comprise a polymeric material containing less than 50% liquid by weight. As used herein, the term "substantially fixed" means that variations in the surface, form, or shape of an optic are small in comparison to the variations necessary to induce significant optical aberrations, that is optical aberrations that are greater than about 10 times the diffraction limited.

Typically, the deformable optic 42 and/or the rigid optic 44 of the IOL 20 are made of foldable material to allow insertion of the IOL 20 through an incision in the eye 22 that is less than about 5 mm in diameter, more preferably less than about 3 mm in diameter, and even more preferably less than about 2 mm in diameter. As used herein, the term "foldable optic" means an optic that is sufficiently pliable to be rolled, folded, compressed, or otherwise deformed for insertion into an incision that is smaller than the diameter of the optic, and is sufficiently resilient to return to substantially its original shape and/or provide substantially the same optical characteristic that the lens had prior to insertion into the eye. As used herein, the term "deformable optic" means an optic having a least one surface configured so that at least a portion of that surface changes shape when subjected to an ocular force or a force in the range of about 0.1 gram to about 100 grams.

As used herein, the term "rigid" refers to the ability of a structure to resist changes in form resulting from ocular forces thereon, for example, the ability of a lens or surface to resist changes in the radius of curvature, the thickness, and/or the asphericity thereof. As used herein, the terms "deformable" refer to the ability of a structure to change form resulting from ocular forces thereon. The terms "rigid" and "deformable" are used herein to refer to the relative rigidity or deformability of one of the rigid optic 44 as compared to that of the deformable optic 42. These terms do not generally refer to the rigidity or deformability of the optics 42, 44 in an absolute sense. Typically, both optics 42, 44 are at least somewhat deformable in the sense that they may be resiliently bent or folded for insertion into the eye 22 so as to reduce the amount of trauma to the eye 22 during a surgery and the healing time after the surgery.

The rigid optic 44 may also be made of one of the more resiliently deformable materials listed above for the deformable optic 42, so long as the final composition or construction of the rigid optic 44 is more rigid than that of the deformable optic 42. For example, both the rigid optic 44 and the deformable optic 42 may be made of acrylic materials. In such embodiments, acrylic material used to form the rigid optic 44 may be made stiffer than that used to from the deformable optic, for example, by making the rigid optic 44 thicker than the deformable optic 42, by increasing the degree of polymerization of the material used to form the rigid optic 44 relative to that of the deformable optic 42, or by forming the rigid optic 44 from a type of acrylic material that is stiffer than that used to form the deformable optic 42.

The materials used to form the optics 42, 44 typically have refractive indices that allow fabrication of relatively thin and flexible optics. Each of the optics 42, 44 may have a thickness in the range of about 150 microns or less to about 1500 microns or more, preferably in the range of about 150 microns to about 500 microns. In order to provide greater rigidity, the rigid optic 44 typically has a center thickness that is greater than the center thickness of the deformable optic 42. Each of the optics 42, 44 typically has a diameter that is about 4.5 mm or less to about 6.5 mm or more, preferably from about 5.0 mm to about 6.0 mm. In certain embodiments, the center thickness of the rigid optic 44 is thicker than the center thickness of the deformable optic 42 especially if both the optics 42, 44 are made of the same material or materials having the same stiffness when formed into the same structure or shape.

The optics 42, 44 may generally take any of the lens forms known in the art, either prior to or after the deformable surface 52 and the rigid surface 54 are pressed together. For example, either of the optics 42, 44 may be a biconvex lens, a biconcave lens, a plano-convex lens, a plano-concave lens, or a meniscus lens. The optical power of each of the optics 42, 44 may be either positive or negative. Alternatively, the optical power of one of the optics 42, 44 may be positive, while the optical power of the other is negative. In certain embodiments, the general form of the deformable optic 42 may change after the surfaces 52, 54 are pressed together. For example, the deformable optic 42 may be a plano-convex lens prior to pressing the surfaces 52, 54 together and a biconvex lens after pressing the surfaces 52, 54 together.

The combined refractive optical power of the optics 42, 44 is preferably within a range of about +5 Diopters to at least about +50 Diopters, more preferably within a range of at least about +10 Diopters to at least about +40 Diopters, and even more preferably within a range of at least about +15 Diopters to at least about +30 Diopters. The most preferred range is that typical of IOLs used in aphakic eyes, for instance after cataract surgery. In other embodiments, the combined refractive optical power of the optics 42, 44 may be within a range of about +5 Diopters about −5 Diopters, or less.

In certain embodiments, the rigid optic 44 is configured to either increases or decreases radius of curvature of the deformable surface 52 when the surfaces 52, 54 are pressed together. Typically, the surfaces 62, 63 of the rigid optic and/or the surface 60 opposite the deformable surface 52 are configured to maintain a fixed or substantially fixed shape when the surfaces 52, 54 are pressed together. The shape of any of the surfaces 60-63 of the optics 42, 44 may either spherical or flat, either prior to or after the deformable and rigid surfaces 52, 54 are pressed together. Alternatively, at least one of the surfaces 60-63 of the optics 42, 44 may be an aspheric surface or have an asymmetric surface, either prior to or after the deformable and rigid surfaces 52, 54 are pressed together. For instance, the profile or shape of at least one of the surfaces 60-63 may be parabolic or some other aspheric shape for reducing an aberration such as a spherical aberration. For example, one or more of the surfaces 60-63 may be an aspheric surface that is configured to reduce spherical aberrations based on either an individual cornea or group of corneas, for example, as described by Piers et al. in U.S. Pat. No. 6,609,673 and U.S. patent application Ser. No. 10/724,852, which are herein incorporated by reference.

In certain embodiments at least one of the optics 42, 44 comprises a diffractive surface, either prior to or after the deformable and rigid surfaces 52, 54 are pressed together. For instance, at least one of the surfaces 60-63 of the optics 42, 44 may comprise a diffractive surface that is configured to correct an aberration of the deformable optic 42, the rigid optic 44, the IOL 20, and/or the eye 22. For example, the diffractive surface may be configured to correct a chromatic aberration, as described in U.S. Pat. No. 6,830,332, which is herein incorporated by reference. The diffractive surface may be configured to cover the entire or substantially the surface of at least one of the surfaces 60-63, either prior to or after the deformable surface 52 and the rigid surface 54 are pressed together. Alternatively, the diffractive surface may cover only a portion of at least one of the surfaces 60-63, for example as described in U.S. Pat. Nos. 4,881,804 and 5,699,142, which is herein incorporated by reference. In other embodiments, a portion of one of the surface 60-63 having the diffractive surface may be configured to provide an optical power that is different from the optical power of a remaining portion of the surface 60-63 that does not contain a diffractive component.

In other embodiments, at least one of the optics 42, 44 is able to provide more than one optical power, for example, a bifocal or multifocal lens, either prior to or after the deformable surface 52 and the rigid surface 54 are pressed together. This may be accomplished by varying the refractive power of one of the surfaces 60-63 as a function of radius from the optical axis 50, for example, as described in U.S. Pat. Nos. 4,898,461 and 5,225,858, which are herein incorporated by reference. Alternatively or additionally, the one or more of the surfaces 60-63 may contain a diffractive surface in which two or more diffractive orders are used to provide two or more optical powers, for examples, as discussed in U.S. Pat. Nos. 4,642,112 and 5,121,979, which are also herein incorporated by reference.

In certain embodiments, at least one of the surfaces 52, 54 comprise a multifocal and/or diffractive surface that is configured to correct an optical aberrations provide more than one focus, and/or provide some other desired optical effect when the surfaces 52, 54 are separated (e.g., not pressed together). In such embodiments, the correction or effect produced by the multifocal and/or diffractive surface may be reduced or eliminated when the surfaces 52, 54 are pressed together, either in response to or in the absence of an optical force. In other embodiments, the rigid surface 54 comprises a multifocal and/or diffractive surface that is configured to correct an optical aberration, provide more than one focus, and/or provide some other desired optical effect when the surfaces 52, 54 are pressed together. In such embodiments, the correction or effect produced by the multifocal and/or diffractive surface may be reduced or eliminated when the surfaces 52, 54 are separated from one another.

The materials and/or surface profiles of the deformable optic 42, the rigid optic 44, and/or the stiffening layer 78 may be advantageously selected to correct an optical aberration of the IOL 20 or the eye 22. For example, the IOL 20 may be used to correct a chromatic aberration, wherein the deformable optic 42 is made of a first material and the rigid optic 44 is made of a second material. In such embodiments, the refractive index and/or Abbe number of the first material is selected to be different from that of the second material, while the radius of curvature of anterior and posterior surfaces 62, 63 of the rigid optic 44 are preferably selected so that the rigid optic 44 has either a positive or negative optical power. Those of skill in the art are able to select the optical powers of the optics 42, 44 and the materials thereof such that the chromatic dispersion of one of the optics is combined with chromatic dispersion of the other optic to provide reduced chromatic aberrations and a combined optical power that is substantially equal over a range of wavelengths. The two optics 42, 44 may be configured to correct a chromatic aberration or some other optical aberration either before or after deformation of the deformable optic 42 caused when the surfaces 52, 54 are pressed together.

Alternatively or additionally, the stiffening layer 78 may be made of a material having a refractive index or Abbe number that is different from that of the deformable optic 42 and/or the rigid optic 44 in order to correct for a chromatic aberration some other aberration of the IOL 20 or the eye 22. In such embodiments, the stiffening layer 78 comprises anterior and posterior surfaces 79, 80 that are preferably selected so that stiffening layer 78 has either a positive or negative optical power. It will be appreciated that the center thickness of the stiffening layer 78 may be considerably greater than or considerably less than the thickness illustrated in FIGS. 4 and 5, either in an absolute sense or relative to the center thickness of the deformable lens 42 along the centerline 50. In other embodiments, the optical power, refractive index, and/or Abbe number of the stiffening layer 78, the deformable optic 42, and the rigid optic 44 may be selected so that the IOL 20 is able correct for a chromatic aberration or other optical aberration when the deformable optic 42 is either in a deformed or undeformed state.

In some embodiments, the rigid optic 44 may also be used to protect and/or strengthen the posterior surface of the capsular bag 32. In this and other embodiments, the rigid optic 44 may be a meniscus lens having either positive or negative optical power, depending on the relative curvatures of the anterior and posterior surfaces 62, 63 of the rigid optic 44. Alternatively, the rigid optic 44 may have no optical power or substantially no optical power. For example, in the illustrated embodiment, the rigid optic 44 forms a meniscus lens in which the radius of curvature of the surface 62 is selected to be substantially equal to that of the surface 63, so that rays from light entering the rigid optic 44 experiences substantially no net bending as the rays passing through the rigid optic 44. In such embodiments, a slight amount of bending may take place, for example, due to imperfections in or stresses on the rigid optic 42, for example due to an ocular force.

In certain embodiments, the support structure 28 comprises one or more haptics 70 having a proximal end 72 that is attached to the deformable optic 42 and distal end 74. The haptics 70 may be formed integrally with the deformable optic 42 and/or the rigid optic 44. Alternatively, the haptics 70 may be separately attached to the deformable optic 42 and/or the rigid optic 44 using any of the methods or techniques known in the art. Typically, the support structure 48 is made of a material that is stiffer or more rigid than either or both of the optics 42, 44, although any combination of relative stiffness between the support structure 48 and the deformable and/or rigid optics 42, 44 is possible.

The haptics 70 are typically fabricated from a material that is biologically inert in the intended in vivo or in-the-eye environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In general, the haptics 70 may comprise any material exhibiting sufficient supporting strength and resilience for maintaining at least one of the optics 42, 44 in the center of the eye 22 and for moving the optics 42, 44 relative to one another in the presence of an ocular force.

Figure 6:
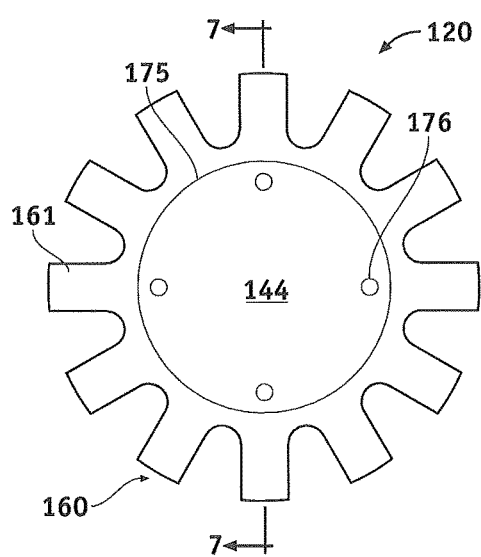
FIG. 6 is a front view of accommodative IOL according to a second embodiment of the invention.
Figure 7:
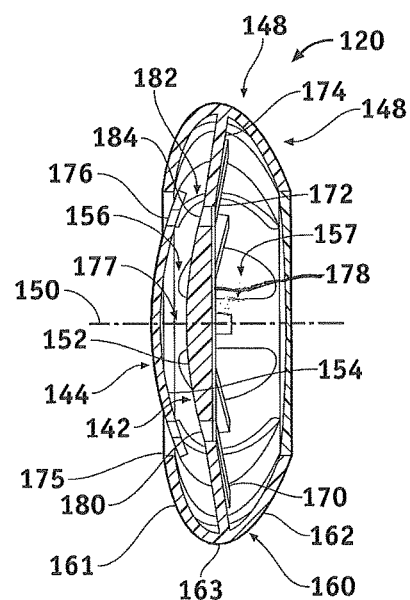
FIG. 7 is a side view of the accommodative IOL illustrated in FIG. 6.

Referring to FIGS. 6 and 7, in certain embodiments, an IOL 120 comprises a deformable optic 142, a rigid optic 144, and a support structure 148 that are disposed about an optical axis 150. The deformable optic 142 comprises a deformable surface 152, while the rigid optic 144 comprises a rigid surface 154. Typically, the support structure 148 is operably coupled to the deformable optic 142 and is configured for pressing the deformable surface 152 and the rigid surface 154 together either in response to an ocular force or in the absence of an ocular.

The support structure 148 comprises an optic positioning element 160 having an anterior segment 161 configured for yieldable engagement with an anterior capsule 34, a posterior segment 162 for yieldable engagement with a posterior capsule 36, and an equatorial segment 163 disposed between the anterior segment 161 and the posterior segment 162. The positioning element 160 is typically constructed such that the equatorial segment 163 is in contact with an equatorial portion of the capsular bag 32 as it changes shape in response to the application or removal of an ocular force. In addition, the optic positioning element 160 is preferably configured to fill or to substantially fill the entire capsular bag 32, such that when an ocular force is applied or removed, a change in the shape of the capsular bag 32 produces a change in the shape of the optic positioning element 160 that causes the deformable surface 152 and the rigid surface 154 to be pressed together. The deformable optic 142 and the rigid optic 144 are configured such that the deformable surface 152 is deformed when the optics 142, 144 are pressed together, typically by at least about 1 Diopter, preferably by at least 2 Diopters, more preferably by 3 Diopters, and even more preferably by at least 4 or 5 Diopters.

The support structure 148 further comprises a plurality of arms 170 for transferring an ocular force on the optic positioning element 160 to the deformable optic 142. In the illustrated embodiment in FIG. 7, each of the arms 170 comprises a proximal end 172 connected to the deformable optic 142 that may be either integrally formed therewith or formed separately and attached to the optic 142. Each of the arms 170 further comprises distal ends 174 that may be connected to the optic positioning element 160 at or near the equatorial segment 163 and that may be either integrally formed optic positioning element 160 or formed separately and attached thereto. In other embodiments, the arms 170 may be connected to some other portion, of the optic positioning element 160, for example to the posterior segment 162. These and other configuration for attaching the arms 170 to the optic positioning element 160 are further illustrated in U.S. patent application Ser. Nos. 10/280,937 and 10/634,498, both of which are herein incorporated by reference.

The rigid optic 144 is typically attached or operably coupled to the optic positioning element 160 at an opening 175 in the anterior segment 161 so as to prevent decentering of the rigid optic 144 relative to the optical axis 150. The rigid optic 144 is typically disposed within the optic positioning element 160 and adjacent to the anterior segment 161.

The optic positioning element 160 may be configured to comprise a front interior chamber 156 formed by the boundaries of the rigid optic 144, the deformable optic 142, and the inner walls of the optic positioning element 160. The optic positioning element 160 may further comprise a rear interior chamber 157 formed by volume within the boundaries of the deformable optic 142 and the inner walls of the optic positioning element 160.

To facilitate the fluid flow or fluid communication between the front interior chamber 156 and the posterior chamber 26 of the eye 22, the rigid optic 144 may comprises a plurality of through holes or openings 176 that are typically disposed at or near the periphery of the rigid optic 144. In certain embodiments, fluid flow into or out of the front interior chamber 156 is additionally or alternatively provided by offsetting the rigid optic 144 posteriorly along the optical axis 155 from the interior wall of the anterior segment 161. One such configuration is illustrated, for example, by FIGS. 7, 8, and 10 of U.S. patent application Ser. No. 10/280,937. In order to facilitate fluid flow or fluid communication between the front and rear interior chambers 156, 157, the deformable optic 142 typically comprises one or more openings or through holes 180. Preferably, at least some of the through holes 176 of the rigid optic 144 are aligned with or overlap with at least some of the through holes 180 of the deformable optic 142.

The deformable optic 142 may further comprise a stiffening layer 178 disposed adjacent to the deformable optic 142 opposite the deformable surface 152. When the deformable optic 142 and the rigid optic 144 are pressed together, the stiffening layer 178 may be used to prevent or inhibit deformation of the surface of the deformable optic 142 that is opposite the deformable surface 152. In certain embodiments, deformation of the surface opposite the deformable surface 152 may be further reduced or eliminated when the surface 152, 154 are pressed together by a relief portion 182 for providing a volume into which material from the deformable optic 142 may flow, enlarge or expand. The relief portion 182 may be disposed about the periphery of the deformable optic 142, for example, as illustrated in FIGS. 4 and 5 for the deformable optic 42. Additionally or alternatively, the relief portion 182 may comprise one or more voids or opening 184 within the body of the deformable optic 142. The openings 184 may be the same as the openings 176 for providing fluid communication between the rear interior chamber 157 and the rest of the eye 22. Alternatively, at least some of the openings 184 used for providing relief during deformation of the deformable optic 142 may be different from at least some of the openings 180 for providing fluid communication between interior chambers 156, 157.

In certain embodiments, the deformable optic 142 is disposed behind the rigid optic 144 and in close proximity therewith when the surfaces 152, 154 are not pressed together. In certain embodiments, there is a gap 177 along the optical axis 150 between the deformable optic 142 and the rigid optic 144 when the surfaces 152, 154 are not pressed together. In such embodiments, the size of the gap 177 may be selected to allow a predetermined amount of axial travel of the deformable optic 142 before it engages the rigid optic 144. In other embodiments, the gap 177 is substantially zero or there is no gap 177, in which case the deformable optic 142 may touch the rigid optic 144 when the surfaces 152, 154 are not pressed together. In such embodiments, the deformable optic 142 may be disposed to only touches the rigid optic 144 at a point substantially along the optical axis 150.

Figure 8:
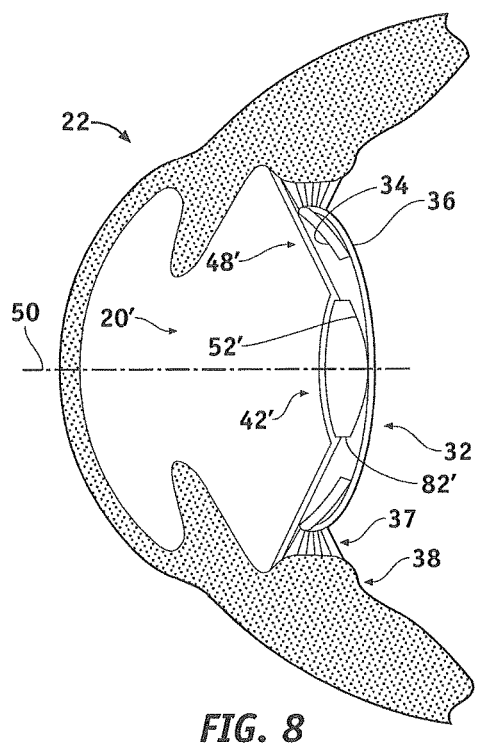
FIG. 8 is a side view of accommodative IOL according to a third embodiment of the invention shown within an eye in an accommodative state.
Figure 9:
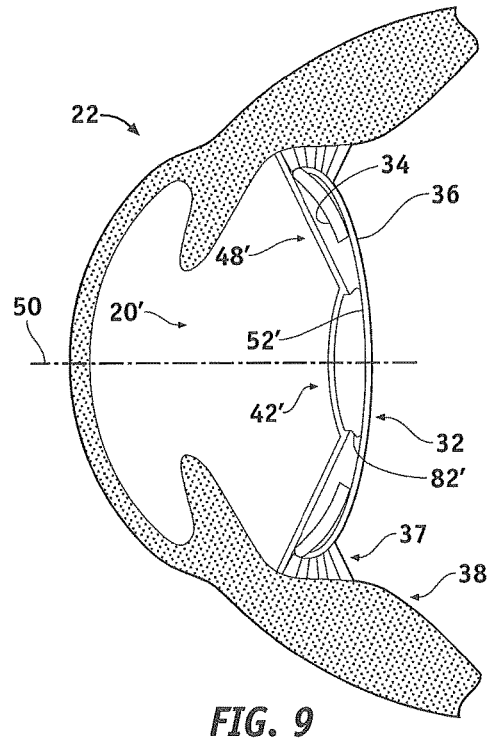
FIG. 9 is a side view of the accommodative IOL illustrated in FIG. 8 shown within an eye in a disaccommodative state.

Referring to FIGS. 8 and 9, in certain embodiments, an IOL 20' comprises a deformable optic 42' and a support structure 48', but does not include a rigid optic such as the rigid optic 44 of the IOL 20. In such embodiments, the support structure 48' is operably coupled to the deformable optic 42' for pressing a deformable surface 52' and at least one surface of the capsular bag 32 (e.g., the anterior capsule 34 and/or the posterior capsule 36) of the eye 22 together in response to or in the absence of an ocular force, whereby at least a portion of the deformable surface 52' changes shape such that the optical power of the at least a portion of the deformable surface 52' and/or the IOL 20' changes, typically by at least about 1 Diopter, preferably by at least 2 Diopters, more preferably by 3 Diopters, and even more preferably by at least 4 or 5 Diopters. In such embodiments, the IOL 20' preferably also comprises a relief portion 82' for providing a volume into which material from the deformable optic 42' may flow, enlarge or expand when the deformable surface 52' is deformed.

Figure 10:
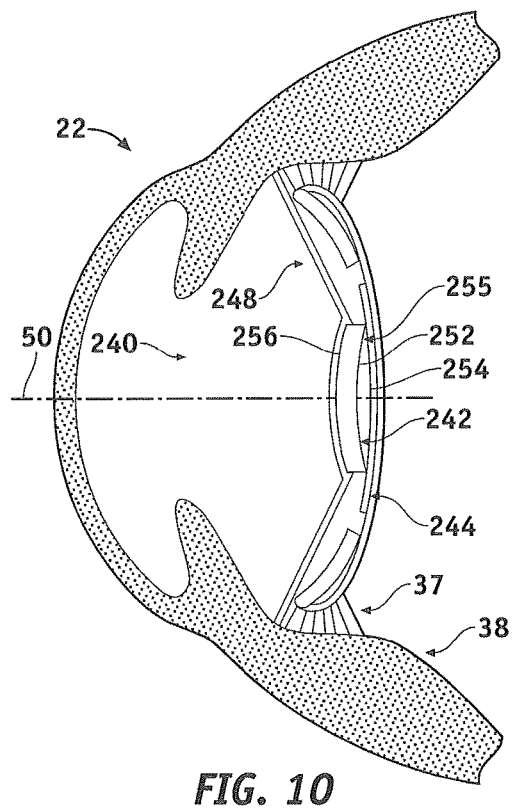
FIG. 10 is a side view of an IOL according to a fourth embodiment of the invention shown within an eye in a disaccommodative state.
Figure 11:
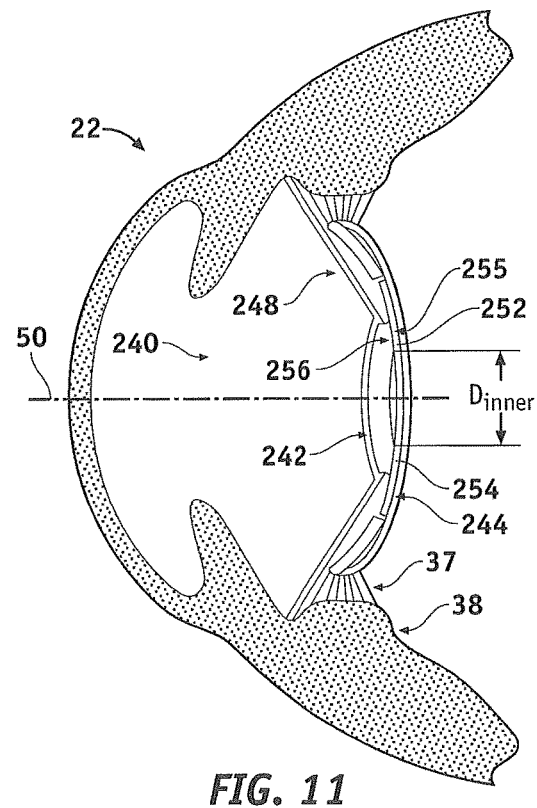
FIG. 11 is a side view of the accommodative IOL illustrated in FIG. 10 shown within an eye in an accommodative state or partially accommodative state.

Referring to FIGS. 10 and 11, in certain embodiments, an IOL 220 comprises a deformable optic 242 having a deformable surface 252 and a rigid optic 244 having a rigid surface 254, the optics 242, 244 being disposed about the optical axis 50 of the eye 22. In such embodiments, only a portion 255 of the deformable surface 252 changes shape when the deformable surface 252 and the rigid surface 254 are pressed together in response to or in the absence of an ocular force, whereby only a portion of light entering the IOL 220 and/or the deformable optic 242 experiences a change in optical power. The optic 240 may further comprise a support structure 248 that is operably coupled to the deformable optic 242. Alternatively, in other embodiments, the support structure 248 may be operably coupled to the rigid optic 244 or to both the deformable optic 242 and the rigid optic 244. The IOL 240 and the deformable optic 242 may be configured to have a disaccommodative bias, as illustrated in FIG. 10. Alternatively, the IOL 240 may have an accommodative bias, depending upon various factors such as the particular physiology of eye 22 and the particular operational outcome desired by the practitioner and/or designer.

In certain embodiments, the deformable surface 252 is concave, as illustrated in FIGS. 10 and 11, in which case the deformable portion 255 is a peripheral portion 256 of the deformable surface 252. In such embodiments, the deformable portion 255 has an inner diameter $D_{inner}$ that is less than about 5 or 6 mm, preferably less than about 4 mm. In certain embodiments, the deformable portion 255 has an inner diameter $D_{inner}$ that is less than about 3 mm. The inner diameter $D_{inner}$ of the deformable portion 255 may be selected based on various factors including the area or percentage of the IOL 220 and/or the deformable surface 252 that is to be directed to near or intermediate vision when the IOL 220 is in an accommodative state. The deformable portion 255 of the IOL 220 may advantageously provide the capability of forming a multifocal lens when the eye 22 is in an accommodative state. In other embodiments, the configuration of the IOL 220 illustrated in FIG. 11 represents a condition in which the eye 22 is only partially accommodated. In such embodiments, the entire or substantially the entire deformable surface 252 is deformed when the eye attains a fully accommodative state.

Figure 12:
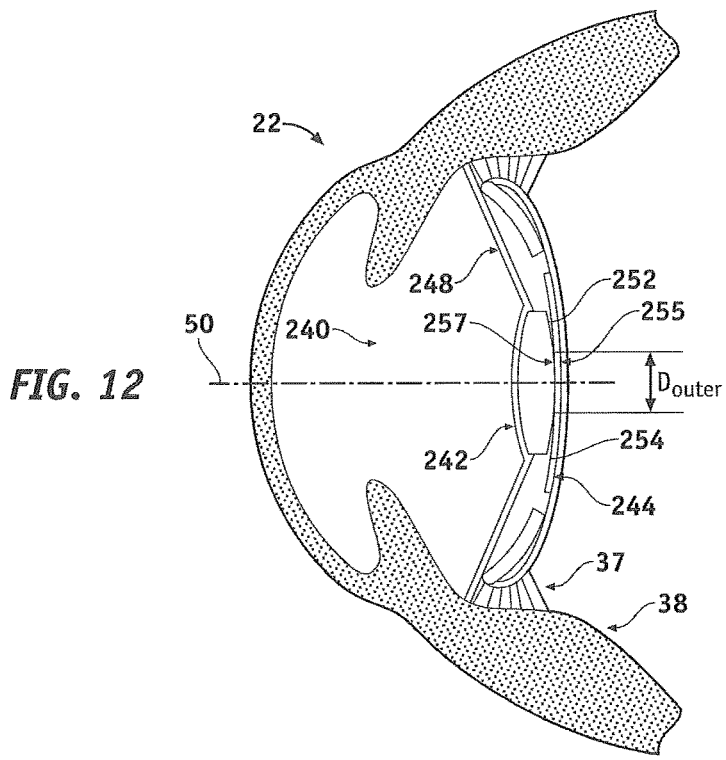
FIG. 12 is a side view of an IOL according to a fifth embodiment of the invention shown within an eye in a disaccommodative state or partially disaccommodative state.

Referring to FIG. 12, in certain embodiments, the deformable optic 242 comprises a deformable surface 252' that is convex. In such embodiments, the deformable portion 255 is a central portion 257 of the deformable surface 252'. In such embodiments, the deformable portion 255 has an outer diameter $D_{outer}$ that is greater than about 1 mm, preferably greater than about 2 mm. In certain embodiments, the deformable portion 255 has an outer diameter $D_{outer}$ that is greater than about 3 mm or 4 mm. The outer diameter $D_{outer}$ of the deformable portion 255 may be selected based on various factors including the area or percentage of the IOL 220 and/or the deformable surface 252 that is to be directed to distant or intermediate vision when the IOL 220 is in an disaccommodative state. The IOL 242 illustrated in FIG. 12 comprises a deformable surface 252' that has a smaller radius of curvature than that of the rigid surface 254 of the rigid optic 244. Alternatively, the deformable surface 252' may have a larger radius of curvature than that of the rigid surface 254. The deformable portion 255 of the IOL 220 illustrated in FIG. 12 may advantageously provide the capability of forming a multifocal lens when the eye 22 is in a disaccommodative state. In other embodiments, the configuration of the IOL 220 illustrated in FIG. 12 represents a condition in which the eye 22 is only partially accommodated. In such embodiments, the entire or substantially the entire deformable surface 252 is deformed when the eye attains a fully disaccommodative state.

Figure 13:
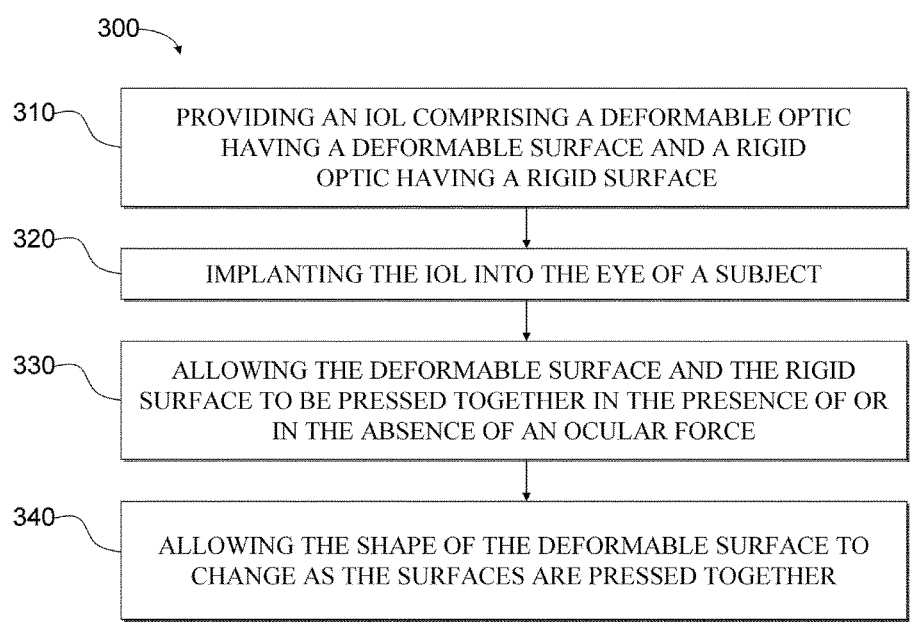
FIG. 13 is flow chart of a method of providing accommodation to a subject according an embodiment of the invention.

Referring to FIG. 13, a method 300 of providing accommodation to a subject will now be discussed using the IOL 120. It will be appreciated that at least portions of the method 300 may be practiced using the IOLs 20, 20', 120, 220, or other IOLs consistent with embodiments of the present invention. The method 300 comprises an operational block 310, which comprises providing the IOL 120. The method 300 additionally comprises an operational block 320, which comprises placing, injecting, or implanting the IOL 120 into the eye 22 of a subject. The method 300 further comprises an operational block 330, which comprises allowing the deformable surface 152 and the rigid surface 154 to be pressed together in response to or in the absence of an ocular force. The method also comprises an operational block 340, which comprises allowing the shape of the deformable surface 152 to change as the surfaces 152, 154 are pressed together such that the optical power of the at least a portion of the deformable surface 152 and/or the IOL 120 changes, typically by at least about 1 Diopter, preferably by at least 2 Diopters, more preferably by 3 Diopters, and even more preferably by at least 4 or 5 diopters.

In certain embodiments, for example in the case of the IOL 20' illustrated in FIGS. 8 and 9, the operational block 320 comprises allowing the deformable surface 52' of the deformable optic 20' and a surface of the capsular bag 32 (e.g., the anterior capsule 34 and/or the posterior capsule 36) to be pressed together in response to or in the absence of an ocular force. In such embodiments, the operational block 330 comprises allowing the shape of the deformable surface to change as the surfaces of the deformable optic 42' and the capsular bag 32 are pressed together such that the optical power of the IOL changes, typically by at least about 1 Diopter, preferably by at least 2 Diopters, more preferably by 3 Diopters, and even more preferably by at least 4 or 5 Diopters. In other embodiments, the operational blocks 330 and 340 together alternatively comprise configuring the support structure 148 for pressing the deformable surface 152 and the rigid surface 154 together in response to an ocular force, whereby at least a portion of the deformable surface 152 changes shape such that the optical power of the intraocular lens changes, typically by at least about 1 Diopter, preferably by at least 2 Diopters, more preferably by 3 Diopters, and even more preferably by at least 4 or 5 Diopters. In general other means consistent with embodiments of the present invention may be used for pressing a deformable surface and a rigid surface together in response to an ocular force, for example, the support structures 48, 48', 148, or 248, the haptics 70, the arms 170.

Figure 14:
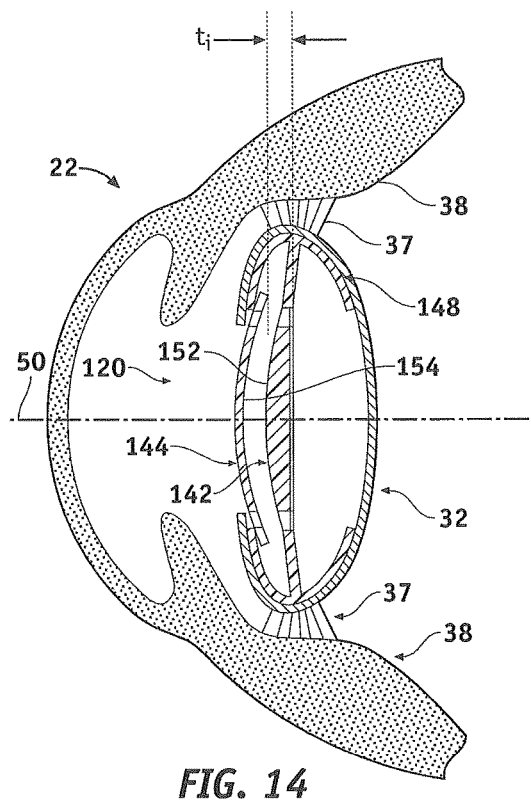
FIG. 14 is a side view of the accommodative IOL illustrated in FIG. 7 shown within an eye in an accommodative state.
Figure 15:
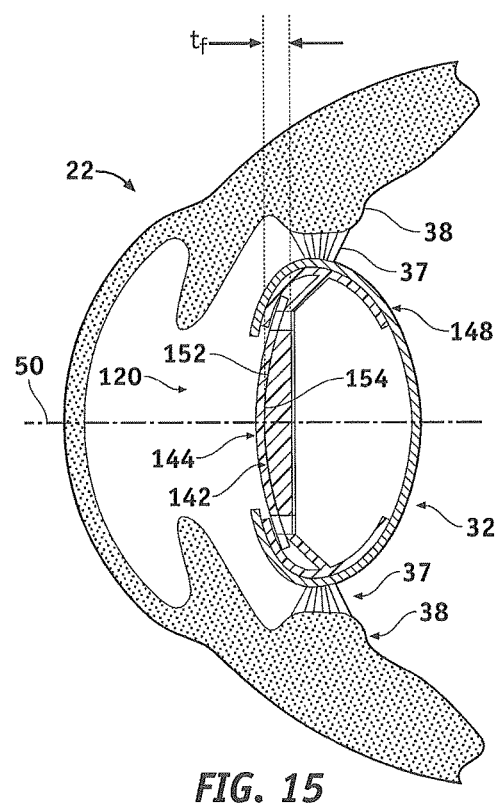
FIG. 15 is a side view of the accommodative IOL illustrated in FIG. 7 shown within an eye in an accommodative state.

With additional reference to FIGS. 7, 14, and 15, in operational block 320, the IOL 120 may be implanted within the capsular bag 32 of the eye 22 using forceps, an inserter or injector device, or some other device or means suitable for the task. Once the IOL 120 is implanted into the eye 22, it may be manipulated until suitably disposed and centered within the eye 22. The entire IOL 120 may be implanted within the eye 22 at one time or, alternatively, different portions of the IOL 120 may be implanted separately and then assembled and configured within the eye 22 as desired. For example, the support structure 148 and the deformable optic 142 may be implanted and suitably disposed within the eye 22, followed by the implantation of the rigid optic 144.

The optics 142, 144 may then be manipulated so that their centers are aligned to one another and with the optical axis 50. Preferably, the support structure 148 is configured to fill or substantially fill the capsular bag 32 when implanted into the eye 22 such that the capsular bag 32 maintains a shape that is at least substantially the same as the shape it had prior to removal of the natural lens.

Portions of the support structure 148 may be attached to the capsular bag 32, for example, through fibrosis with the inner surfaces of the capsular bag 32 (e.g., as disclosed in U.S. Pat. No. 6,197,059, herein incorporated by reference), through the use of a substance such as an amphiphilic block copolymer or tissue intermediate polymer (TIP), or using some other substance, device, or method known within the art. Attachment of the support structure 148 to the capsular bag 32 allows the shape of the support structure 148 to conform to the capsular bag 32 as the capsular bag 32 changes shape in response to forces produced by the ciliary muscle 38 during accommodation. Typically, the shape of the support structure 148 in an unstressed condition is substantially the same as that of the capsular bag 32 when the eye 22 is in either an accommodative state or a disaccommodative state, depending on whether the IOL 120 is configured with an accommodative bias or disaccommodative bias, respectively.

In certain embodiments, the state of accommodation must be controlled and maintained during a period of time in which the support structure 148 is attaching or being attached to the capsular bag 32. This period of time may during the surgical procedure in which the IOL 120 is implanted into the eye 22 and/or during a postoperative period that may last from several minutes or hour to as much as several weeks or months. During this period of time, the state of accommodation of the eye 22 may be controlled using any of the various method known within the art (e.g., U.S. Pat. Nos. 6,197,059, 6,164,282, 6,598,606 and U.S. patent application Ser. No. 11/180,753, all of which are herein incorporated by reference).

Operational blocks 330 and 340 of the method 300 may comprise allowing the surfaces 152, 154 to be pressed together in the response to or in the absence of an ocular force and allowing the shape of the deformable surface 152 to thereby change. As illustrated in FIG. 14, when the ciliary muscle 38 is relaxed or retracted, the capsular bag 32 has a more discoid shape that is substantially the same as the external form or shape of the support structure 148 and the IOL 120 illustrated in FIG. 7. Thus, in this embodiment, the IOL 120 has a disaccommodative bias, since the IOL 120 is in a natural or unstressed state when the eye 22 is in a disaccommodative state. Since the radius of curvature of the deformable surface 152 in FIG. 14 is relatively large, the focal length of the deformable optic 142 and the IOL 120 is relatively long, which corresponds to an eye in the disaccommodative state and is appropriate for providing distant vision.

Referring to FIG. 15, the ciliary muscle 38 is contracted, which causes the capsular bag 32 and the IOL 120 have a more spheroid shape. This change in the shape of the IOL 120 causes the deformable surface 152 of the deformable optic 142 to press against the rigid surface 154 of the rigid optic 144. Advantageously, this pushing together of the deformable and rigid optics 142, 144 cause the radius of curvature of the deformable surface to decrease, which causes the focal length of deformable optic 142 and the IOL 120 to be decreased. This decrease in focal length provides a subject into which the IOL 120 has been implanted the ability to see objects that are relatively closer (e.g., with near or intermediate vision). In addition to decreasing the focal length of the deformable optic 142, the change in shape of the support structure 148 during contraction of the ciliary muscle 38 may also favorably cause the deformable and/or rigid optics 142, 144 to traverse or vault anteriorly along the optical axis 50. This movement of the deformable and/or rigid optics 142, 144 is also beneficial in allowing the subject to see objects that are relatively closer. In some embodiments, this axial travel of at least one of the optics 142, 144 of the IOL 120 may be favorably utilized in combination with deformation of the deformable optic 142 to increase the overall add power of the IOL, thereby increase the accommodative range and/or image quality of the IOL 120 compared to prior art accommodative IOLs.

In certain embodiments, the IOL 120 has an accommodative bias rather than the accommodative bias construction shown in FIG. 7. For example, the IOL 120 may be configured to have the shape or state shown in FIG. 15 when there are no or substantially no external forces acting on the support structure 148. In such embodiments, the eye 22 may be maintained in an accommodative state while the support structure 148 attaches or is attached to the walls of the capsular bag 32. Thus, during accommodation, when the ciliary muscle 38 is contracted, the IOL 120 is in its natural or unstressed state in which deformable surface 152 is pressed against the rigid surface 154 of the rigid optic 144. By contrast, when the ciliary muscle is retracted or relaxed, tension on the zonules 37 is reduced, allowing the capsular bag 32 to have the more discoid shape shown in FIG. 14. The discoid shape of the capsular bag 32 produces an ocular force on the IOL, 120 that changes the shape of the support structure 148, which causes the deformable surface 152 (and deformable optic 142) to retract or pull away from the rigid surface 154 (and the rigid surface 144). Since the deformable surface 152 is no longer pressed against the rigid optic 144 under these conditions, the deformable surface 152 returns to its original shape and radius of curvature increases, as illustrated in FIG. 14. The increase in the radius of curvature cause the focal length of the deformable optic 142 and the IOL 120 to decrease. This condition of the IOL 120 and the eye 22 may also move the deformable and/or the rigid optics 142, 144 posteriorly along the optical axis 50. Both these effects, the decreased focal length of the deformable optic 142 and the posterior axial movement of the deformable and/or rigid optics 142, 144, may be used to produce a disaccommodative condition or provide distant vision in which a subject is better able to focus on more distant objects.

In yet other embodiments, the IOL 120 has neither an accommodative nor a disaccommodative bias. For example, the IOL 120 may be configured to provide intermediate vision that allows a subject to focus on objects located at some intermediate distance. In such embodiments, the eye 22 may be maintained in an intermediate state between near and distant vision as the support structure is attached or attaches to the capsular bag 32.

The IOL 120 may be configured to produce one or more of a variety of changes in the deformable optic 142 and/or the deformable surface 152 when the surfaces 152, 154 are pressed together. For example, as discussed above, the radius of curvature of the deformable surface 152 may be changed as the surfaces 152, 154 are pressed together. The change in the radius of curvature may be used to produce a change the optical power of the IOL 120 that is positive (a positive add power), for instance when the IOL 120 is configured to have a disaccommodative bias. Alternatively, the change in the radius of curvature may be used to produce a change the optical power of the IOL 120 that is negative, for instance when the IOL 120 is configured to have an accommodative bias. Typically, the change in optical power of the IOL 120 is at least about 1 or 2 Diopters or more.

In certain embodiments, the change in optical power is not simply a positive or negative change. For instance, the support structure 148 may be used to convert the deformable optic 142 from a single focus optic to a multifocal lens comprising refractive and/or diffractive features to produce a plurality of focal lengths or images. For example, the deformable surface 152 of the deformable optic 142 may be fabricated with a spherical surface profile, while the rigid optic 144 may be configured in the form of a meniscus lens in which both anterior and posterior surfaces have a multifocal type profile that is substantially the same. Since both surfaces of the rigid optic 144 are substantially the same, it would have little or no optical power in and of itself. However, as the surfaces 152, 154 are pressed together, the shape of the deformable surface 152 would conform to multifocal profile of the rigid surface 154 and thus change from an optic producing a single focus or image to one producing a plurality of foci or images.

In other embodiments, the deformable optic 142 has a center thickness $t_i$ along the optical axis when in a substantially unstressed state and a center thickness $t_f$ in the response to or in the absence of an ocular force, wherein the surfaces 152, 154 of the deformable optic 142 and the rigid optic 144 are pressed together. In such embodiments, the deformable optic 142 may be adapted to change the center thickness by a factor of at least 1.1 (e.g., the quotient $t_f/t_i$ is at least 1.1), typically when the ocular force is in the range of about 1 to 9 grams, preferably in the range of about 6 to 9 grams. In other embodiments, the deformable optic 142 is adapted to change the center thickness by a factor of at least 1.05 or at least 1.2 or more. In yet other embodiments, the deformable optic 142 is adapted to change the center thickness by a factor of at least 1.05, 1.1, or 1.2 when the ocular force is in the range of about 1 to 3 gram. In still other embodiments, the deformable optic 142 has a center thickness along the optical axis when the deformable optic 142 is in a substantially unstressed state, the deformable optic adapted to change the center thickness by at least about 50 micrometers, preferably at least 100 micrometers, when the ocular force is in the range of about 1 to 9 grams, in the range of about 6 to 9 grams, or in the range of about 1 to 3 grams. Within the art, an understanding of the physiology of the eye is still developing. Thus, other ranges of ocular forces able to provide the above ranges of relative and/or absolute thickness change are anticipated as the physiology of the eye is better understood. Such ranges of ocular forces are also consistent with embodiments of the present invention as disclosed herein.

In certain embodiments, the method 300 further comprises allowing correction of an optical aberration of the deformable optic 142 and/or the eye 22 either in response to or in the absence of an ocular force. For example, the deformable surface 152 may be allowed to change from a substantially spherical surface when the eye 22 is in an unaccommodated state to an aspheric surface as the surfaces 152, 154 are pressed together. This may be accomplished by fabricating the rigid surface 154 with an aspheric profile that changes the deformable surface 152 as the surfaces 152, 154 are pressed together. The change in the deformable surface 152 may be used to reduce or eliminate one or more optical aberrations of the deformable surface 152, the deformable optic 142, the IOL 20, and or the entire eye 22. In other embodiments, the deformable surface 152 is fabricated with an aspheric profile that reduces aberrations when the IOL 120 is in a first state (e.g., an accommodative or disaccommodative state) and is deformed when the surfaces 152, 154 are pressed together to have a different aspheric profile that reduces aberrations when the IOL 120 is in a second state that is different from the first state.

The IOL 120 shown in FIGS. 7, 14, and 15 is configured to have an anterior vault when the surfaces 152, 154 of the deformable and rigid optics 142, 144 are pressed together. In other embodiments, the method 300 may be used wherein an IOL according to embodiments of the invention produces a posterior vault when the deformable and rigid surfaces are pressed together.

For example, referring again to FIGS. 2 and 3, the IOL 20 is configured to have a posterior vault, since contraction of the ciliary muscle 38 causes the deformable optic 42 to move in the posterior direction along the optical axis 50. Referring to the operational block 320, the IOL 20 may be implanted into the eye 22 such that at least a portion of the support structure 28 is configured for placement in the sulcus 39, allowing the IOL 20 to respond directly to contractions of the ciliary muscle 38. As illustrated in FIG. 1, the distal ends 74 of the haptics 70 may be operably coupled to sulcus 39 such that they are substantially fixed within the sulcus 39 as the ciliary muscle contract and retracts. The distal ends 74 may be attached to the eye 22 through fibrosis, through the use of a substance such as an amphiphilic block copolymer, or through some other means known in the art. Typically, the remaining portions of the haptics 70 are relatively free to move in response to ocular forces and are used to change the shape, radius of curvature, and/or thickness of the deformable optic 42 as the optics 42, 44 are, pressed together.

Referring to the operational blocks 330 and 340, the use of the IOL 20 in providing accommodation may be demonstrated using FIGS. 2 and 3. FIG. 2 illustrates the IOL 20 in its natural or unstressed state in which the posterior surface 61 of the deformable optic 42 has a relatively short radius of curvature and, consequently, a relatively short focal length and a relatively high optical power. This configuration of the IOL 20 corresponds to an accommodative state of the eye 20 in which the ciliary muscle 38 is contracted. The deformable optic 42 in this accommodative state is preferable either proximal to the rigid optic 44 or lightly contacts the rigid optic 44 at or near the optical axis 50.

By contrast, FIG. 3 illustrates the form of IOL 20 when the eye 22 is in a disaccommodative state that is produced when the ciliary muscle 38 is retracted. In this disaccommodative state, the ocular force on the IOL 20 pushes the rigid optic 44 toward the deformable optic 42. This causes the radius of curvature of the deformable optic 42 to increase and become the same, as or at least closer to, the radius of curvature of the rigid surface 54 of the rigid optic 44. This increase in the radius of curvature causes the IOL 20 to have a relatively large radius of curvature, so that the IOL 20 has the relatively low optical power desirable to produce a disaccommodative state. In addition, the deformable optic 42 and/or the rigid optic 44 may move anteriorly along the optic axis 50 as the eye 22 changes from the accommodative state illustrated in FIG. 2 to the disaccommodative state illustrated in FIG. 3. This axial movement of the deformable and rigid optics 42, 44 may advantageously allow the IOL 20 to provide a greater accommodative range than is available using other prior art accommodative lenses that do not utilize both optic shape change and axial travel.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out, and distinctly claim the subject matter of the invention.

What is claimed is:

1. An intraocular lens, comprising:
    a deformable optic disposed about an optical axis comprising a deformable surface;
    a rigid optic disposed about the optical axis comprising a rigid surface; and
    a support structure operably coupled to at least one of the optics for pressing the deformable surface and the rigid surface together in response to an ocular force, whereby at least a portion of the deformable surface changes shape, and wherein the deformable optic and the rigid optic are separated by a gap along the optical axis when the deformable optic and the rigid optic are not pressed together;
    wherein the deformable optic further comprises a relief portion around a periphery of the deformable optic for providing a volume into which a portion of the deformable optic may flow, expand, or enlarge only when the deformable surface is pressed against the rigid surface.

2. The intraocular lens of claim 1, wherein the intraocular lens has an optical power when the deformable optic and the rigid optic are separated and wherein the optical power is at least 2 Diopters different when the deformable surface and the rigid surface are pressed together.

3. The intraocular lens of claim 1, wherein the deformable surface and the rigid surface are pressed together when an external ocular force in the range of about 1 to 9 grams is applied to the support structure.

4. The intraocular lens of claim 1, wherein the deformable surface is in contact with, and conforms to, the rigid surface when the deformable surface and the rigid surface are pressed together.

5. An intraocular lens, comprising:
    a deformable optic disposed about an optical axis, the deformable optic having a deformable surface;
    a rigid optic disposed about the optical axis comprising a rigid surface; and
    a support structure operably coupled to at least one of the optics for pressing the deformable surface and the rigid surface together in the absence of ocular forces, whereby at least a portion of the deformable surface changes shape by increasing or decreasing an area of contact of the deformable and rigid optics adjacent to the optical axis, and wherein the deformable surface and the rigid surface are separated by a gap along the optical axis when the deformable surface and the rigid surface are not pressed together;
    wherein the deformable optic further comprises a relief portion around a periphery of the deformable optic for providing a volume into which a portion of the deformable optic may flow, expand, or enlarge only when the deformable surface is pressed against the rigid surface.

6. The intraocular lens of claim 5, wherein the support structure configured to change the shape of the at least a portion in response to an ocular force as the deformable surface moves away from the rigid surface.

7. The intraocular lens of claim 5, wherein the intraocular lens has an optical power when the deformable optic and the rigid optic are separated and wherein the optical power is at least 2 Diopters different when the deformable surface and the rigid surface are pressed together.

8. The intraocular lens of claim 5, wherein the deformable surface is in contact with, and conforms to, the rigid surface when the deformable surface and the rigid surface are pressed together.

9. An intraocular lens, comprising:
    a deformable optic disposed about an optical axis comprising a deformable surface;
    a rigid optic disposed about the optical axis comprising a rigid surface; and
    a support structure having a distal end and a proximal end, the proximal end being attached to the deformable optic for producing a force that presses the deformable surface and the rigid surface together and into contact in response to an ocular force such that at least a portion of the deformable surface is deformed and substantially conforms to the shape of the rigid surface, and wherein the deformable surface and the rigid surface are separated by a gap along the optical axis when the deformable surface and the rigid surface are not pressed together;
    wherein the deformable optic further comprises a relief portion around a periphery of the deformable optic for providing a volume into which a portion of the deformable optic may flow, expand, or enlarge only when the deformable surface is pressed against the rigid surface.

10. The intraocular lens of claim 9, wherein the intraocular lens has an optical power when the deformable optic and the rigid optic are separated and wherein the optical power is at least 2 Diopters different when the deformable surface and the rigid surface are pressed together.

11. The intraocular lens of claim 9, wherein the deformable surface and the rigid surface are pressed together when an external ocular force in the range of about 1 to 9 grams is applied to the support structure.

12. An intraocular lens, comprising:
    a deformable optic disposed about an optical axis comprising a deformable surface;
    a rigid optic disposed about the optical axis comprising a rigid surface; and
    a support structure having a distal end and a proximal end, the proximal end being attached to the deformable optic for pressing the deformable surface and the rigid surface together and into contact in an area disposed adjacent the optical axis in response to an ocular force, whereby only a portion of the deformable surface changes shape, and wherein the deformable surface and the rigid surface are separated by a gap along the optical axis when the deformable surface and the rigid surface are not pressed together;
    wherein the deformable optic further comprises a relief portion around a periphery of the deformable optic for providing a volume into which a portion of the deformable optic may flow, expand, or enlarge only when the deformable surface is pressed against the rigid surface.

13. The intraocular lens of claim 12, wherein the intraocular lens has an optical power when the deformable optic and the rigid optic are separated and wherein the optical power is at least 2 Diopters different when the deformable surface and the rigid surface are pressed together.

14. The intraocular lens of claim 12, wherein the deformable surface and the rigid surface are pressed together when an external ocular force in the range of about 1 to 9 grams is applied to the support structure.

15. The intraocular lens of claim 12, wherein the deformable surface is in contact with, and conforms to, the rigid surface when the deformable surface and the rigid surface are pressed together.

16. An intraocular lens, comprising:
a deformable optic disposed about an optical axis comprising a deformable surface;
a rigid optic disposed about the optical axis comprising a rigid surface characterized by a radius of curvature; and
a support structure having a distal end and a proximal end, the proximal end being attached to the deformable optic;
the rigid optic and the deformable optic defining a clear aperture that includes the optical axis and through which light incident upon optics forms a focus;
the deformable surface having, within the clear aperture, a first shape and a second shape, the first shape including a surface portion having a finite radial extent and characterized by a radius of curvature unequal to the radius of curvature of the rigid surface, the second shape being characterized over the surface portion by a radius of curvature that is equal to the radius of curvature of the rigid surface;
wherein the second shape is provided when the support structure presses the deformable surface and the rigid surface together and brings into contact a portion of the deformable surface with a portion of the rigid surface adjacent the optical axes thereof, and wherein the deformable surface and the rigid surface are separated by a gap along the optical axis when the deformable surface and the rigid surface are not pressed together;
wherein the deformable optic further comprises a relief portion around a periphery of the deformable optic for providing a volume into which a portion of the deformable optic may flow, expand, or enlarge only when the deformable surface is pressed against the rigid surface.

17. The intraocular lens of claim 16, wherein the first shape has a first optical power and the second shape has a second optical power over the surface portion that is at least 2 Diopter different than the first optical power.

18. The intraocular lens of claim 16, wherein the second shape is provided when an external ocular force in the range of about 1 to 9 grams is applied to the support structure.

19. The intraocular lens of claim 16, wherein the surface portion is in contact with, and conforms to, the rigid surface when the deformable surface has the second shape.

20. The intraocular lens of claim 16, wherein the deformable optic has the second shape when the intraocular lens is in a natural state in which there are no external forces on the intraocular lens.

* * * * *